United States Patent
Lewy et al.

[11] Patent Number: 5,731,512
[45] Date of Patent: Mar. 24, 1998

[54] METHOD FOR QUICK ESTIMATION OF ERYTHROCYTE SEDIMENTATION RATE WITH CAPILLARY TUBES LINED WITH PREFORMED ANTICOAGULANT, MOUNTED IN AN OBLIQUE POSITION, AND SUPPORTED ON A SPECIALLY DESIGNED STAND

[76] Inventors: Henry Lewy, deceased, late of Jerusalem; by Elsa Lewy, heiress, P.O. Box 18331, Ramat Eshkol 91181, Jerusalem, both of Israel

[21] Appl. No.: 714,467

[22] Filed: Sep. 16, 1996

[51] Int. Cl.$^6$ .............. G01N 15/04; G01N 33/48; B01D 37/04
[52] U.S. Cl. .............. 73/61.65; 73/64.41; 436/69; 436/70; 210/513; 422/73; 422/101
[58] Field of Search .............. 73/61.65, 61.66, 73/61.63, 64.41; 356/39, 40, 246; 436/70, 69; 210/803, 513; 422/73, 101

[56] References Cited

U.S. PATENT DOCUMENTS

| | | | |
|---|---|---|---|
| 2,729,971 | 1/1956 | Stein | 73/61 |
| 3,026,717 | 3/1962 | Danielsson et al. | 73/61 |
| 3,373,601 | 3/1968 | Monn | 73/61.4 |
| 3,434,859 | 3/1969 | Benjamin | 117/17 |
| 3,734,079 | 5/1973 | Weber | 128/2 G |
| 3,812,966 | 5/1974 | Beach et al. | 210/70 |
| 4,045,175 | 8/1977 | Weber | 23/230 B |
| 4,474,056 | 10/1984 | O'Brien et al. | 73/61.4 |
| 4,477,574 | 10/1984 | Silander | 436/70 |
| 4,622,847 | 11/1986 | Paoletti et al. | 73/61.4 |
| 4,848,900 | 7/1989 | Kuo et al. | 356/39 |
| 5,594,164 | 1/1997 | Bull | 73/61.66 |

*Primary Examiner*—Michael Brock
*Assistant Examiner*—J. David Wiggins

[57] ABSTRACT

An improved method for the estimation of Erythrocyte Sedimentation Rate (ESR), with capillary tubes lined with preformed anticoagulant, in an oblique position, on a specially designed stand. The method utilizes the property of whole blood to sediment faster in an oblique position but avoids cumbersome mixing of blood and requirements for special equipment. Standard anticoagulant coated capillary tubes are allowed to fill with blood to a predetermined length by capillary action and the tubes are then placed on a specially designed stand for standardized readings of the final blood plasma/erythrocyte cell interface level after 10 minutes. The method enables the physician to obtain information with regards to the ESR within a short time as during consultation or a house call.

1 Claim, 1 Drawing Sheet

METHOD FOR QUICK ESTIMATION OF ERYTHROCYTE SEDIMENTATION RATE WITH CAPILLARY TUBES LINED WITH PREFORMED ANTICOAGULANT, MOUNTED IN AN OBLIQUE POSITION, AND SUPPORTED ON A SPECIALLY DESIGNED STAND

CROSS REFERENCES TO RELATED APPLICATIONS

Weber Ragnar, U.S. Pat. No. 4,045,175,–Aug. 30, 1977. Other cited references

Linzenmeyer and Eyer, 1934, Muench. Med. Wschr., 81; 174.

BACKGROUND OF THE INVENTION

1. Field of the Invention

This method relates to the quick estimation of Erythrocyte Sedimentation Rate (ESR) using a capillary tube lined with anticoagulant mounted in an oblique position, thereby accelerating the rate of sedimentation of red blood corpuscles.

2. Description of Related Art

There have been several methods for the estimation of the Erythrocyte Sedimentation Rate:

1. The standard method of Erythrocyte Sedimentation Rate, as recommended by the International Committee for Standardization of Hematology 1973 per the universal Westergren sedimentation test, consists of the dilution of whole blood with a solution of trisodium titrate (3.1 g/100 cc) in the proportion of 4 parts blood to 1 part citrate, and putting the mixture into a graduated pipette of 200 mm length, in an upright position. The fall of the erythrocytes within the blood column is measured after 60 minutes.

2. A micro-method of determining erythrocyte sedimentation, by introducing a blood sample into a vertical capillary tube having an anticoagulant heparin coating on the interior surface thereof. Time required for reading results: 75 minutes (as per teachings of Weber Ragnar 1977, U.S. Pat. No. 4,045,175).

3. Method of Linzenmeyer and Eyer (as described in the prior art reference of Muench. med. Wschr. 81,174, 1934), using a capillary pipette which has to be filled first with sodium citrate solution. The capillary pipette includes a dilated mixing chamber for mixing the blood with the sodium citrate solution. Blood is drawn into the pipette by capillary action and is then sucked into the mixing chamber to be mixed with the sodium citrate solution. The pipette is then put in an oblique position. Time required for reading results: 10 minutes.

SUMMARY OF THE INVENTION

The object of the invention consists in combining two of the afore mentioned methods for estimating the Erythrocyte Sedimentation Rate;

a) in a capillary tube with preformed anticoagulant, as coating applied on the tube wall, b) in an oblique position, obtaining thereby a) easy preparation,—b) quick results.

The novelty of the invention is based on the fact that it avoids the Linzenmeyer and Eyer method step involving a cumbersome mixing of the sodium citrate solution in a specially constructed mixing chamber with the blood because the blood is drawn directly into the capillary tube. By placing the tube in an oblique position (instead of vertically) results can be obtained in a relatively short time. The method is thus made amenable for the physician to obtain information on the ESR during consultation or a house call, without cumbersome manipulations.

DESCRIPTION OF THE PREFERRED EMBODIMENT

Figure 1:
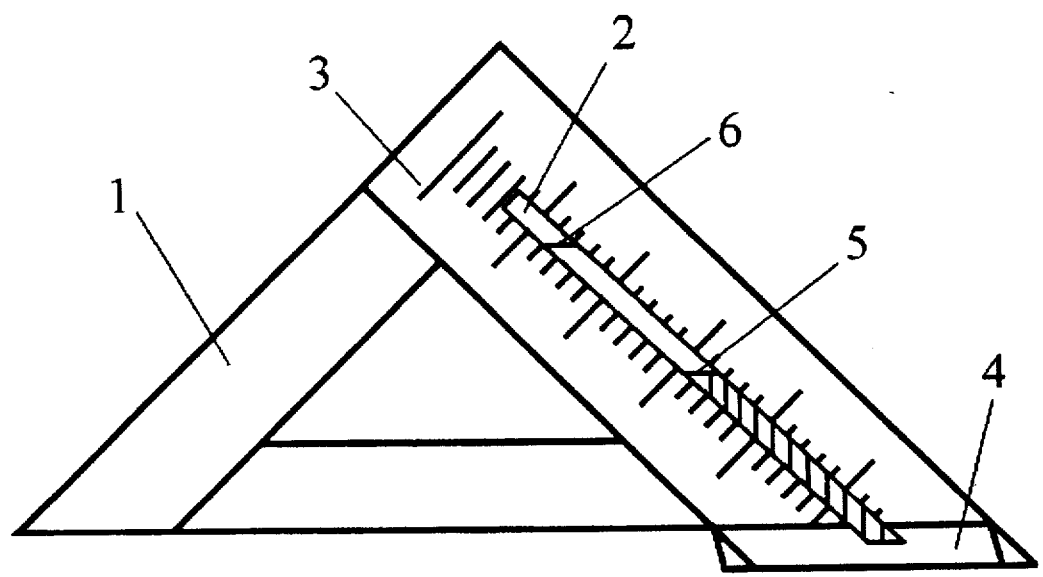
FIG. 1 shows a side view of the device as described in the preferred embodiment. A stand (1) made in the shape of an isosceles triangle serves as support for a capillary tube (2). The flattened surface of the triangle on which the capillary rests includes a graduated scale (3) and the capillary is placed on a platform extension containing a sealant cement (4) to prevent blood leakage. In the drawing the original blood column which was drawn into the capillary has separated to a sedimented erythrocyte column (5) and plasma (6).
Figure 2:
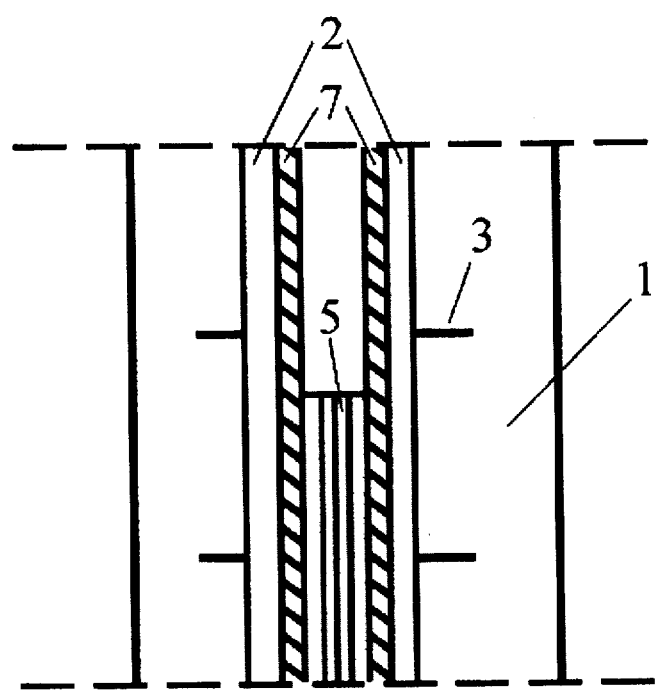
FIG. 2 shows an expanded view in cross section of the capillary at the region of the plasma/erythrocytes interface. The capillary is coated internally with an anticoagulant (7) and the markings on the graduated scale (3) indicate the height of the erythrocyte column (5) within the capillary (2).

The technique is as follows:

A minimal amount of blood (which may be taken from the finger) is drawn by capillary action into a capillary tube (2) lined with heparin or some other anticoagulant (7), up to a predetermined length (e.g. 70 mm). The tube is then placed on a specially designed stand (1) that has graduated scale markings thereon (3) and is designed to orient such tube with an inclination of 45°. A lip or protrusion of the stand containing an appropriate sealing cement (4) serves as a mounting platform for placement of the capillary at ground level and to stop leakage of the blood. The fall of the Erythrocyte column (5) within the capillary is measured after 10 minutes so as to determine the final position of the blood plasma (6)/erythrocyte (5) interface level relative to such graduated markings on the support stand.

I claim:

1. An improvement in the Linzenmeyer and Eyer method for estimation of Erythrocyte Sedimentation Rate (ESR) without need of a mixing step in a mixing chamber of a capillary pipette, which comprises by taking in by capillary action a minimal amount of whole blood directly into a capillary tube lined inside with a preformed anticoagulant coating such as heparin which then forms a blood column within said capillary tube up to a predetermined length of some 70 mm, and putting it on a dedicated stand with a mounting surface therewith and with a set of graduated (millimeter) scale markings thereon to provide reference measurement levels, where said dedicated stand further orients the capillary tube in an oblique position having an inclination of 45 degrees from horizontal attitude, and then,—reading the fall of the erythrocytes in the blood column after a short time (of usually 10 minutes) by a medical technician or physician making a visual comparison of the blood plasma/erythrocyte sediment layer interface against the reference levels of said graduated scale markings on said dedicated stand.

* * * * *